US011684821B2

(12) United States Patent
Abecassis et al.

(10) Patent No.: US 11,684,821 B2
(45) Date of Patent: Jun. 27, 2023

(54) VIRTUAL ATHLETIC COACH

(71) Applicant: Humango, Inc., Wilmington, DE (US)

(72) Inventors: Eric Raphael Abecassis, Boulder, CO (US); William Cleveland Tidwell, Smyrna, GA (US); Alan Robert Couzens, Erie, CO (US)

(73) Assignee: Humango, Inc., Wilmington, DE (US)

( * ) Notice: Subject to any disclaimer, the term of this patent is extended or adjusted under 35 U.S.C. 154(b) by 197 days.

(21) Appl. No.: 17/118,223

(22) Filed: Dec. 10, 2020

(65) Prior Publication Data

US 2021/0178226 A1 Jun. 17, 2021

Related U.S. Application Data

(60) Provisional application No. 62/946,502, filed on Dec. 11, 2019.

(51) Int. Cl.
| | |
|---|---|
| *A63B 24/00* | (2006.01) |
| *G16H 20/30* | (2018.01) |
| *G06F 16/215* | (2019.01) |
| *A63B 71/06* | (2006.01) |
| *G06F 16/23* | (2019.01) |

(52) U.S. Cl.
CPC ...... *A63B 24/0075* (2013.01); *A63B 71/0622* (2013.01); *G06F 16/215* (2019.01); *G06F 16/2379* (2019.01); *G16H 20/30* (2018.01); *A63B 2024/0068* (2013.01); *A63B 2071/0694* (2013.01); *A63B 2225/50* (2013.01)

(58) Field of Classification Search
USPC ........................................................ 434/29
See application file for complete search history.

(56) References Cited

U.S. PATENT DOCUMENTS

| 8,784,115 | B1 | 7/2014 | Chuang | |
|---|---|---|---|---|
| 10,518,163 | B2* | 12/2019 | Lee | .................. G16H 40/63 |
| 10,599,816 | B2* | 3/2020 | Orenstein | ............... G01W 1/10 |
| 10,957,448 | B2* | 3/2021 | Orenstein | ............... G01W 1/10 |
| 2010/0179027 | A1 | 7/2010 | McGlynn et al. | |
| 2010/0184563 | A1 | 7/2010 | Molyneaux et al. | |
| 2012/0173978 | A1* | 7/2012 | Lee | .................. A63B 71/0686 |
| | | | | 715/716 |
| 2013/0040272 | A1 | 2/2013 | Booher | |
| 2015/0324751 | A1* | 11/2015 | Orenstein | ............... G16H 40/67 |
| | | | | 702/3 |

(Continued)

OTHER PUBLICATIONS

"International Search Report and Written Opinion Issued in PCT Application No. PCT/US2020/064316", dated Mar. 4, 2021, 13 Pages.

*Primary Examiner* — Pierre E Elisca
(74) *Attorney, Agent, or Firm* — Holzer Patel Drennan

(57) ABSTRACT

Some existing health and fitness apps map athletic activity and track that activity over time and present to the athlete various aggregations of their activity. Other existing health and fitness apps create training schedules for the athlete to achieve a fitness goal. However, the training schedules provided by these apps are static in nature and provide a fixed quantity and type of exercise within a fixed schedule for the athlete to accomplish. The presently disclosed virtual athletic coach offers dynamic training schedules that can make incremental adjustments based on an athlete's performance to the training schedule over time.

20 Claims, 10 Drawing Sheets

(56) References Cited

U.S. PATENT DOCUMENTS

2015/0375085 A1   12/2015  Molyneaux et al.
2017/0329934 A1* 11/2017  Orenstein ............... G01W 1/10
2019/0299059 A1   10/2019  Case, Jr. et al.

* cited by examiner

VIRTUAL ATHLETIC COACH

CROSS-REFERENCE TO RELATED APPLICATIONS

The present application claims benefit of priority to U.S. Provisional Patent Application No. 62/946,502, entitled "Virtual Athletic Coach", and filed on Dec. 11, 2019, which is specifically incorporated by reference herein for all that it discloses or teaches.

BACKGROUND

Athletes are increasingly using mobile and/or wearable devices (e.g., smart phones, smart watches, etc.) to aid in their personal lives, including helping them achieve their health and fitness goals. A variety of mobile applications (also referred to herein as apps) currently exist to monitor athlete health and fitness. However, as mobile and/or wearable devices become increasingly advanced, athletes expect more out of their health and fitness apps.

Some existing health and fitness apps have the capability to map athletic activity (e.g., generate a map of a running circuit), and track that activity over time and present to the athlete various aggregations of their activity. These apps may also connect to the athlete's social media network and share the athlete's athletic activity with other athletes. Other existing health and fitness apps create training schedules for the athlete to achieve a fitness goal (e.g., a specific training schedule to train the athlete to run a marathon). However, the training schedules provided by these apps are static in nature and provide a fixed quantity and type of exercise within a fixed schedule for the athlete to accomplish. Some existing health and fitness apps provide a link between an athlete and their coach. These apps permit the athlete and/or their coach to build a training plan for the athlete within the app, monitor the athlete's progress in achieving the training plan via the app, and manually modify the athlete's training program based on their performance over time.

SUMMARY

Implementations described and claimed herein address the foregoing problems by providing a method of providing virtual athletic coaching comprising generating a fatigue profile for a user, generating a fitness profile for the user, collecting stated goals and life constraints from the user, inputting the fatigue profile, the fitness profile, the stated goals, and the life constraints into a user optimization engine, and generating a training plan for the user to achieve the stated goals within the life constraints based on the fatigue profile and the fitness profile.

Other implementations are also described and recited herein.

BRIEF DESCRIPTIONS OF THE DRAWINGS

DETAILED DESCRIPTIONS

Even when an athlete utilizes an experienced coach to create, monitor, and revise a training plan for the athlete over time, the human mind cannot adequately process the number of constraints and potential solutions. As a result, a human coach will necessarily over-simply the constraints and potential solutions, apply the human coach's natural bias to solutions that the human coach has previously witness work, and fail to optimize a training plan for the athlete to a level achievable with the presently disclosed technology.

Further, existing health and fitness apps lack the ability to dynamically adjust the athlete's training program based on various feedback criteria to optimize the athlete's training program to achieve stated goal(s). The presently disclosed health and fitness app (also referred to herein as a virtual athletic coach) for mobile, and/or wearable devices prescribes a solution for an athlete to achieve stated goal(s) and dynamically adjusts the prescribed solution over time according to an array of feedback criteria. Further, the virtual athletic coach may similarly prescribe a solution for a human user that is not specifically an athlete to achieve stated health and fitness goal(s), such as weight loss, endurance, and longevity. Accordingly, an athlete as used herein may be any human user of the virtual athletic coach. In still further implementations, the presently disclosed virtual athletic coach may be executed on other computing devices outside of mobile and/or wearable devices (e.g., on a personal computer).

An example implementation of the virtual athletic coach may offer dynamic training schedules that can make incremental adjustments based on an athlete's performance to the training schedule over time. For example, the virtual athletic coach may lower the recommended training session duration, frequency of training sessions, and/or extend the training period if the athlete is falling behind schedule. Similarly, the virtual athletic coach may increase the recommended training session duration, frequency of training sessions, and/or shorten the training period if the athlete is ahead of schedule. The virtual athletic coach works for range of athletes from novices to professionals.

Figure 1:
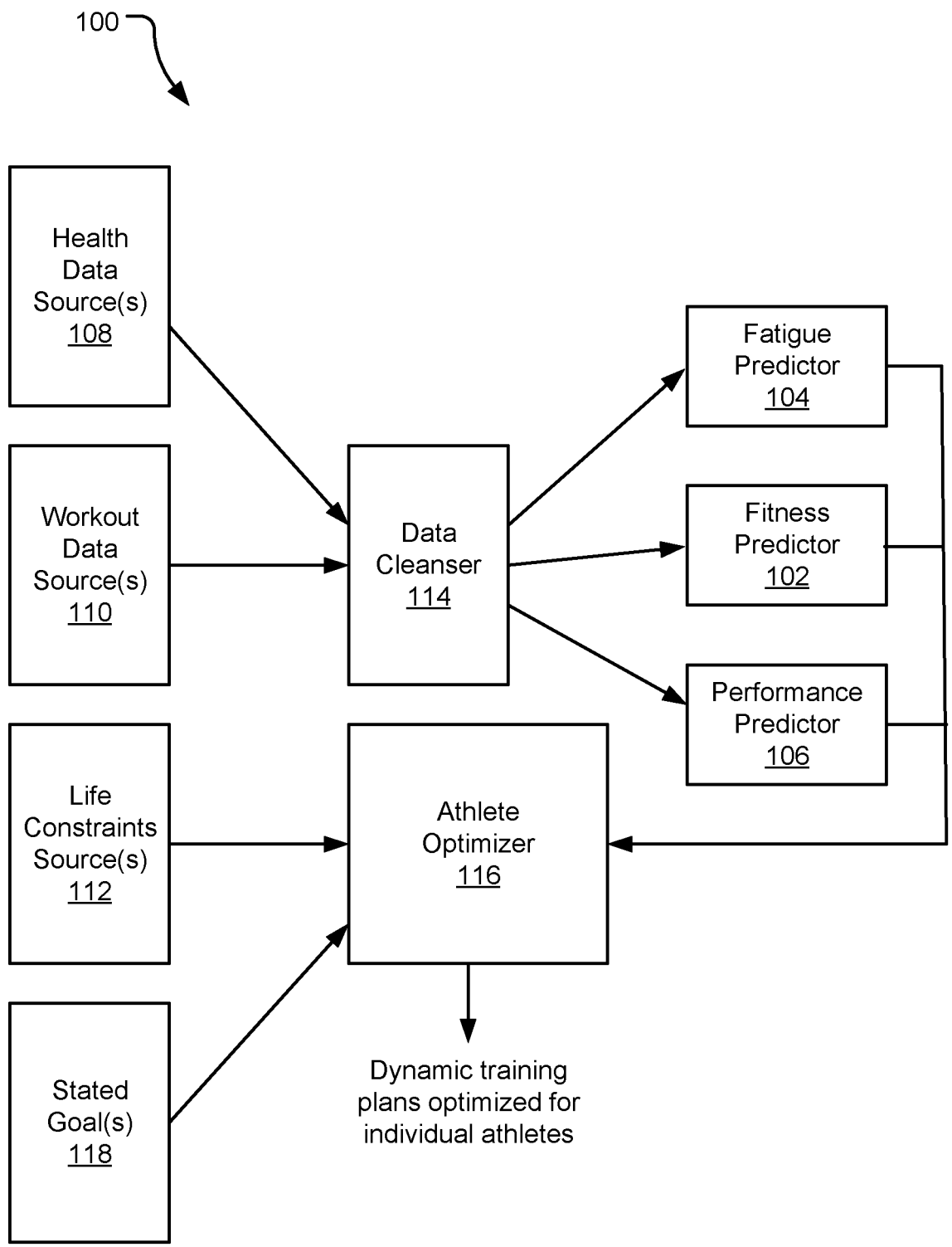
FIG. 1 illustrates an example flow diagram for an optimization engine for a virtual athletic coach.

FIG. 1 illustrates an example flow diagram for an optimization engine 100 for a virtual athletic coach (also referred to as a health and fitness app). The virtual athletic coach provides an interface for interaction with the athlete and/or their human coach, including data collection from the athlete and a dynamic training plan output to the athlete and/or their coach. The optimization engine 100 analyzes data collected from and regarding the athlete via the virtual athletic coach to run one or more distinct predictors and an athlete optimizer 116. More specifically, the distinct predictors (e.g., a fitness predictor 102, a fatigue predictor 104, and a performance predictor 106) use input data from one or more distinct sources (e.g., health data source(s) 108 and workout data source(s) 110).

The health data source(s) 108 may include various data collected manually and automatically from the athlete, and well as objective and subjective data regarding the athlete's overall state of health. In an example implementation, the athlete wears a fitness tracking device that automatically collects the athlete's vital statistics (e.g., sleep quality, resting heart rate, heart rate during training sessions, heart rate variation (HRV), stress levels, etc.) and activities (e.g., a step counter, global positioning system (GPS) movement tracking, etc.). The athlete may also manually enter into the virtual athletic coach additional vital statistics that are not collected by the fitness tracking device (e.g., the athlete's height, weight, body mass index, body type, etc.). The athlete may further manually enter into the virtual athletic coach subjective data regarding the athlete's health (e.g., an indication of the athlete's overall state of being, such as: happy, content, or unhappy; healthy, recovering, or sick; no, low, moderate, or high pain level.

The workout data source(s) 110 may include various data collected manually and automatically from the athlete, as well as objective and subjective data regarding the athlete's workouts. In an example implementation, the athlete's fitness tracking device automatically collects statistics on workouts that the athlete performs while wearing the fitness tracking device (e.g., workout type (such as swimming, bicycling, or running, if detectable), intensity, duration, etc.). The athlete may also manually enter into the virtual athletic coach additional workout data that was not collected by the fitness tracking device (e.g., the workout type (if not detected by the app), details regarding additional workouts performed by the athlete when not wearing the fitness tracking device). The athlete may further manually enter into the virtual athletic coach subjective data regarding the athlete's workouts, such as: an indication of the athlete's enjoyment of a particular workout (e.g., enjoyed, neutral, or did not enjoy); whether the workout caused the athlete pain (e.g., no, low, moderate, or high level of pain); and whether the athlete felt the workout was effective (e.g., not, moderately, or highly effective).

Data collected from the health data source(s) 108 and workout data source(s) 110 is fed into a data cleanser 114 that analyzes the collected data and compares it against expected data. Outlying data (e.g., particularly strange or suspect data) is de-emphasized or removed from the data set. For example, the athlete may perform a workout that is detected by the athlete fitness tracking device (e.g., the GPS detects that the athlete went on a run), however, the heart rate monitor of the fitness tracking device malfunctioned and did not indicate a heart rate within a reasonable range expected for the athlete performing that type of workout. The data cleanser 114 may detect the disparity in data and automatically discard the heart rate data from that particular workout. The data cleanser 114 may also instruct the virtual athletic coach to notify the athlete of the malfunction.

In an example implementation, 60-80% of the most reliable data collected is used to generate an output and the remaining 20-40% of the least reliable data is discarded. Further, as the athlete uses the virtual athletic coach, the data cleanser 114 may modify its expectation to apply specifically to the athlete based on prior data collection. As such, the ability of the data cleanser 114 to determine data reliability may increase over time as the data cleanser 114 better understands patterns in the athlete's data. Further, the data cleanser 114 is able to function and adapt over time without direct input from the athlete. In other implementations, the data cleanser 114 may query the athlete via the app to confirm validity of some or all of the data (e.g., specifically, the outlying data). In some implementations, the data cleanser 114 tags distinct sections of collected data with a reliability indicator. Then, the fitness predictor 102, fatigue predictor 104, and/or performance predictor 106 may use only data that meets reliability threshold(s) specific to the fitness predictor 102, fatigue predictor 104, and/or performance predictor 106.

The fatigue predictor 104 tracks current and past states of fatigue of the athlete and predicts future states of fatigue for the athlete based on past performance and the selected training solution for the athlete. The fatigue predictor 104 tracks fatigue on a scale (e.g., a freshness scale from 0-10 or 0-100%). The fatigue predictor 104 includes at least one model defining the effect of a selected training solution for the athlete on the athlete's state of fatigue (also referred to herein as a load profile). The fatigue predictor 104 also includes at least one model defining the effect of rest and sleep on the athlete's state of fatigue (also referred to herein as a recovery profile). Other factors may be incorporated into one or both of the load profile(s) and recovery profile(s) (e.g., diet, workload outside the selected training solution, etc.). Further, the load profile(s) and recovery profile(s) may be general to a group of athletes and/or specific to each athlete. The fatigue predictor 104 utilizes the load profile and the recovery profile to monitor a current state of fatigue for the athlete and predict the athlete's state of fatigue at various points in time in the future.

The athlete's predicted state of fatigue can then be used to modify the athlete's selected training solution for optimum results. For example, applying a particularly difficult workout to an athlete that is particularly fatigued (e.g., 3 or less on the freshness scale) may not be very effective. Similarly, if the athlete is substantially fresh (e.g., 7 or greater on the freshness scale), a light workout may be replaced with a more difficult workout to obtain better results for the athlete.

The fatigue predictor 104 may predict both short-term (e.g., within a day or a week) and long-term (e.g., beyond a day or a week) states of fatigue. Short-term predicted fatigue may be used to make small corrections to the athlete's workouts to avoid states of over or under fatigue. While confidence in a state of fatigue predicted by the fatigue predictor 104 drops as the projected time period increases, a long-term prediction may still be useful for making large corrections in the athlete's selected training solution to generally avoid states of over or under fatigue. In this manner, the fatigue predictor 104 is used as a simulator for the athlete's state of fatigue given a selected training solution and provides feedback as to whether the selected training solution should be modified for the athlete.

The fitness predictor 102 tracks the athlete's overall fitness changes over time (also referred to herein as a response profile) as a function of the types, intensities, and durations of training that the athlete completes. The fitness predictor 102 can then customize the athlete's selected training solution to take advantage of training types, intensities, and durations that are more effective for the athlete than other training types, intensities, and durations, for example.

Different athletes respond to different types of training differently. For example, some athletes respond better to base training vs. intensity training or strength training vs. cardiovascular training. The fitness predictor 102 tracks the athlete's fitness improvement over time (e.g., using metrics such as lap times, peak strength, etc.) to determine what types, intensities, and durations of training are more effective at moving the athlete toward stated goal(s) than others. The fitness predictor 102 may modify the athlete's selected training solution to emphasize more effective types, intensities, and durations of training over less effective types, intensities, and durations of training.

The performance predictor 106 takes into account the athlete's existing fitness metrics (e.g., lap times, peak strength, total distance, etc.) and a rate and quantity of fitness improvement predicted by the fitness predictor 102 to predict the athlete's ability to achieve a stated goal, and at what level. For example, if the athlete's stated goal is running a marathon on a particular day, the performance predictor 106 will be able to project the athlete's ability to run the marathon, and at what pace, on the given race day. The performance predictor 106 may update the projection as the athlete progresses through the selected training solution, and perhaps offer the athlete positive feedback on how their fitness metrics will likely improve if a given set of workouts within the selected training solution is completed. In an example implementation, the performance predictor 106 is a combination of the athlete's fitness prediction curve and the athlete's power duration curve, accounting for environmental factors both during training and on the given race day.

In an example implementation, each of the predictors 102, 104, 106 utilize an artificial neural network (a recurrent neural network in some implementations) to analyze the input health data and workout date, cleaned by the data cleanser 114, to accurately predict the athlete's response fatigue, and performance as described herein. In further implementations, additional predictors may be included to accurately predict other aspects of the athlete's life. For example, a health predictor may be used to predict one or more health factors for the athlete (e.g., changes in blood pressure) caused by changes in the athlete's diet and execution of the selected training solution.

Athlete optimizer 116 collects the outputs from the fitness predictor 102, the fatigue predictor 104, and the performance predictor 106, and combines them with data from life constraints source(s) 112 and athlete's stated goal(s) 118 to optimize a dynamic training plan specific to the athlete's individual circumstances and stated goal(s) 118. The life constraints source(s) 112 may include various data collected manually and automatically from the athlete, as well as objective and subjective data regarding the athlete's life constraints. In an example implementation, the athlete's fitness tracking device automatically collects some life constraints from the athlete (e.g., typical sleep schedule, work schedule, commute times and durations, etc.). The athlete may also manually enter into the app additional life constraints that are not collected by the fitness tracking device (e.g., scheduled vacations, family and friend time, illnesses, birthdays, anniversaries, holidays, etc.). The athlete may further manually enter into the virtual athletic coach subjective data regarding the athlete's life constraints such as: time of day the athlete is available or prefers to workout (e.g., morning midday, evening, or night) and days of the week the athlete is available or prefers to workout (e.g., weekdays, weekends, or specific days). In some implementations, the athlete optimizer 116 may crawl through the athlete's calendar or other personal data to determine some or all of the athlete's life constraints.

In an example implementation, the virtual athletic coach collects one or more goals from the athlete. Primary goals may include running a marathon, completing a triathlon, overall fitness, longevity, etc. Secondary goals may include utmost performance, injury avoidance, overall health, low overall fatigue, etc. For example, the athlete may have a primary goal of running a marathon and a secondary goal of achieving the primary goal with minimization of risk of injury. Another athlete may also have a primary goal of running the marathon, but a secondary goal of minimizing overall time to complete the marathon.

The athlete optimizer 116 receives the stated goals from the virtual athletic coach and analyzes them in conjunction with the outputs from the predictors 102, 104, 106 and the data from the life constraints source(s) 112 to determine a best training solution to achieve the athlete's stated goal(s). The output from the athlete optimizer 116 is one or more of a day-by-day, week-by-week, or month-by-month training plan, individualized training dose, and/or optimize fatigue/response cycle for the athlete.

As compared to a typical training program, the athlete optimizer 116 is not limited to simple recurring patterns that are common to typical training plans for ease of use. The athlete optimizer 116 can create a complex training plan and meter it out to the athlete on a day-by-day, week-by-week, or month-by-month basis, for example. The athlete optimizer 116 can also provide descriptors corresponding to portions of the training plan (e.g., a muscle breakdown period, a muscle rebuild period, a resting period, etc.) and feedback on the athlete's use of the training plan on a day-by-day, week-by-week, or month-by-month basis, for example.

The athlete optimizer 116 may be used to self-coach the athlete as described above or used in conjunction with a human coach for the athlete. The athlete's human coach may be able to add custom constraints (e.g., only two hard sessions per week) based on the coach's training style and/or specific knowledge of the athlete. The human coach and the athlete may both have access to the virtual athletic coach using the same or similar user interfaces.

In various implementations, the athlete optimizer 116 utilizes a machine learning environment (or a reinforcement learning algorithm or neural network) to balance outputs from the predictors 102, 104, and/or 106, taking into account the athlete's life constraints 112 and stated goal(s) 118. The athlete optimizer 116 attempts to identify an optimal solution of workout types, duration, intensity, and schedule that satisfies the athlete's life constraints 112 to best achieve the athlete's stated goal(s) 118. To reduce processing complexity and time, in some implementations, the athlete optimizer 116 further utilizes a deep learning artificial intelligence (AI) to identify potential solutions that were not attempted by the athlete optimizer 116 and interpolate the likely outcomes of the un-attempted solutions based on the results of the attempted solutions.

Figure 2:
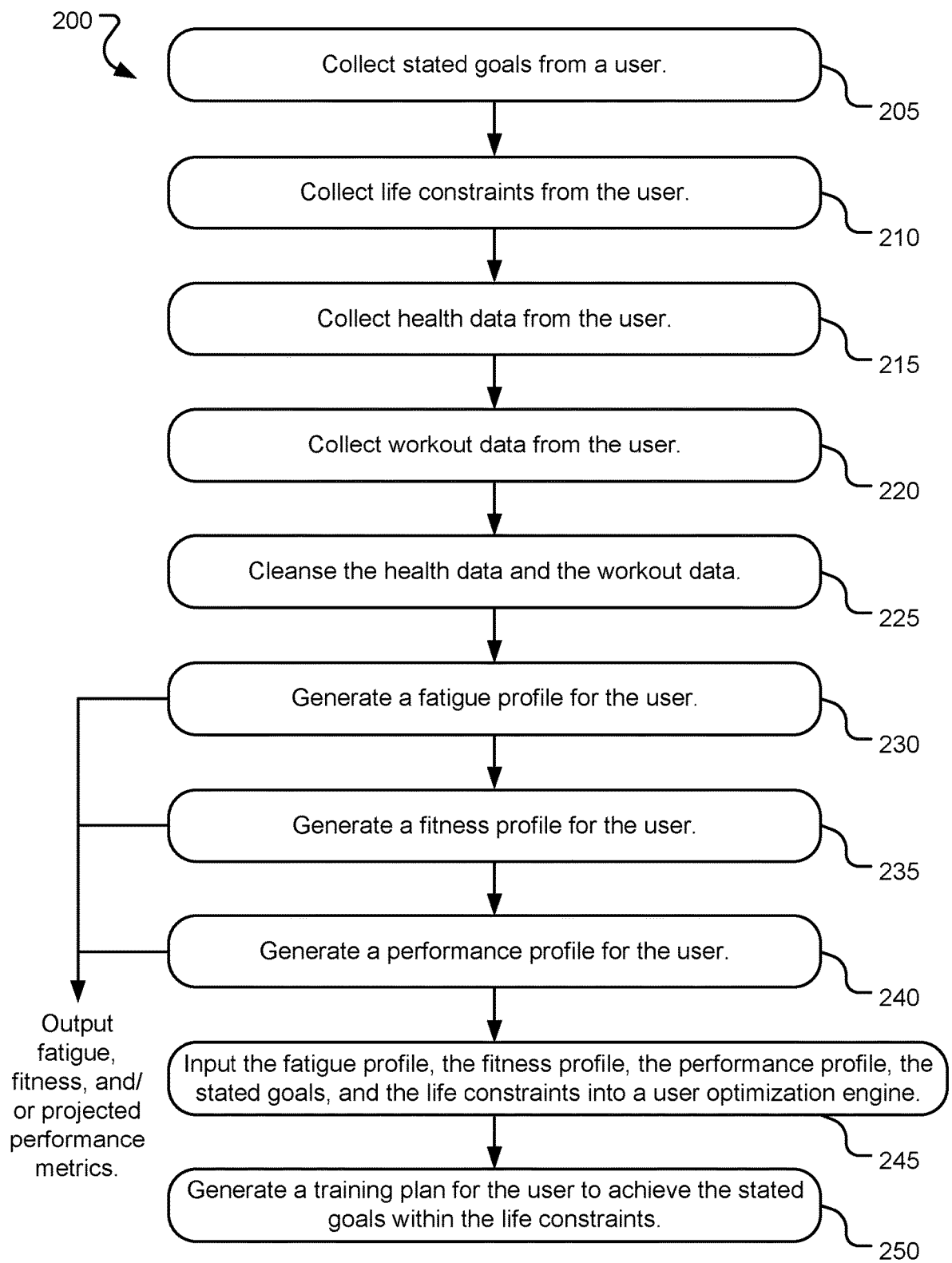
FIG. 2 illustrates example operations for generating a training plan for a user using a virtual athletic coach.

FIG. 2 illustrates example operations 200 for generating a training plan for a user using a virtual athletic coach. Operations 200 are performed using a virtual athletic coach optimization engine (see e.g., optimization engine 100 of FIG. 1) and a virtual athletic coach application (see e.g., user interface screenshots 400, 500, 600, 700, 800, 900 of FIGS. 4-9). A first collecting operation 205 collects stated goals from a user. The stated goals may range from a specific and determine goal, such as running a marathon on a particular date, to general and indeterminate, such as maximizing overall user health and fitness. A second collecting operation 210 collects life constraints from the user. The life constraints provide hard limits on the user's ability or desire to perform a training plan. In various examples, the life constraints include scheduling constraints (due to holidays, vacations, and other work and family life commitments), facility availability constraints (such as days and/or hours of operation for a pool, when swimming is used as a training activity), weather (such as presence of inclement weather when cycling is used as a training activity), injuries (such as limiting to easy-level runs when the user is recovering from a leg injury), preferred training (e.g., specific desired training phases and durations), and so on. The user may enter one or more stated goals and zero or more life constraints, as well as a priority order of the stated goals, into the user interface for the virtual athletic coach. Further, some or all of the life constraints may be provided by a human coach for the user (e.g., preferred training constraints) due to the human's coaches preferences or specific knowledge of the user.

A third collecting operation 215 collects health data from the user. The health data includes biometric and health information regarding the user. This information may include manually entered data, such as the user's age, sex, height, weight, body mass index (BMI), etc., and/or automatically collected information from a wearable device (e.g., resting heartrate, peak heartrate, average activity level, etc.). In the case of a wearable device, the health data may be re-collected and modified automatically over time. A fourth collecting operation 220 collects workout data from the user. The workout data includes information specific to the workouts that the user performs. This information may include manually entered data, such as type, intensity, and duration of a workout that the user performed, and/or similar automatically collected information from the wearable device. Further, the automatically collected information from the wearable device may be used to supplement or further inform the manually entered data regarding the user's workout. Still further, the automatically collected information from the wearable device may be used to detect a workout and remind the user to enter manually entered data regarding the workout. The user may the health data and/or the workout data into the user interface for the virtual athletic coach.

A cleansing operation 225 cleanses the health data and the workout data. As the health data and the workout data may be collected over time, the cleansing operation 225 may average data points within the health data and/or the workout data. This can create a more accurate seed data set for the virtual athletic coach. The cleansing operation 225 may further disregard outlier data points as erroneous data (e.g., lack of a heart rate during a workout due to a failure of the user's wearable device).

A first generating operation 230 generates a fatigue profile for the user. The fatigue profile is specific to the user and estimates the user's fatigue level over time as a function of the user's collected health data and workout data. In one implementation, a standard physiological model for fatigue is used as an initial seed fatigue profile for the user. The standard physiological model for fatigue utilizes inputs for training load and intensity and duration to track changes in the user's fatigue over time. However, for a user that has been using the virtual athletic coach for some time, the fatigue physiological model may be iteratively customized to more closely approximate the user's specific response to a training load, intensity, duration, and the resulting effect on the user's fatigue.

A second generating operation 235 generates a fitness profile for the user. The fitness profile is specific to the user and estimates the user's fitness over time as a function of the user's collected health data and workout data. In one implementation, a standard physiological model for fitness is used as an initial seed fitness profile for the user. The standard physiological model for fitness utilizes inputs for training load and intensity and duration to track changes in the user's fitness over time. However, for a user that has been using the virtual athletic coach for some time, the fitness physiological model may be iteratively customized to more closely approximate the user's specific response to a training load, intensity, duration, and the resulting effect on the user's fitness.

In an example implementation, the following formula, which calculates an exponentially weighted average of the training load experienced by the athlete, is used to define the aforementioned physiological models for fitness and fatigue, respectively, as described above: $CWL=AWL-\text{training load}*(1-\lambda_x)+\text{prevWorkload}*\lambda_x$, where $\lambda_x$ is defined as: $\lambda_x=\exp-1/x$. x is a time constant in days that varies by individual, by sport, and/or by whether fitness or fatigue is being calculated. Default values for the general population have been determined to be x=42 days for fitness and x=7 days for fatigue. The larger value of 42 days for fitness represents a chronic workload (CWL) and includes approximately the last six months of training. The smaller value of 7 days for fatigue represents an acute workload (AWL) and includes approximately the last one month of training.

A third generating operation 240 generates a performance profile for the user. The performance profile is specific to the user and estimates the user's performance over time as a function of the user's collected health data and workout data, as well as the user's fatigue and fitness profiles. Depending on the user's stated goals, the performance profile may be a metric used to measure the user's achievement relative to the stated goals. For example, the user's stated goal may be to run a marathon on a specific date with a lowest possible time. A training plan may be designed for the user's performance profile to peak on the specific date of the marathon to best achieve the user's stated goal of running the marathon with a lowest possible time.

In one implementation, a standard physiological model for performance is used as an initial seed performance profile for the user. The standard physiological model for performance utilizes inputs for fatigue and fitness to track changes in the user's performance over time. However, for a user that has been using the virtual athletic coach for some time, the performance physiological model may be iteratively customized to more closely approximate the user's specific response to fatigue and fitness, and the resulting effect on the user's performance. In various implementations, the performance profile is a calculated balance of the aforementioned fatigue and fitness profiles and includes a calculation of accumulated fatigue.

In an example implementation, a fitness fatigue delta (FFD) (also referred to a training stress balance (TSB)) is used to determine whether the athlete is accumulating or shedding fatigue over time (FFD=CWL−AWL). A negative FFD means that the athlete is performing training sessions with a training load higher than the CWL and is accumulating fatigue. A positive FFD means that the athlete is performing sessions with a training load less than the CWL and shedding fatigue. When trying to build fitness, FFD should be negative, but not too negative. A FFD floor (or minimum FFD) may be used and targeted for the athlete extending periods of training. A FFD ceiling (or maximum FFD) may also be used to allow the athlete to shed fatigue just before a race, for example.

In some implementations, the fatigue, fitness, and/or the performance profiles for the user are used as output(s) to the user. For example, the fatigue and fitness profiles may be used to output a metric indicative of the user's fatigue and fitness on a specific day. For example, on a particular day, the user's fatigue is at a $7/10$ and the user's fitness is at a $5/10$. This may indicate that the user has recently been working hard against their training plan, but it is too early in the training plan for the user's fitness to catch up to their fatigue. Further, the user's performance profile may be used to estimate the user's performance relative to their stated goal(s). For example, the virtual athletic coach may provide a trend in performance if the user continues to perform to their training plan (e.g., the user can expect a 2% increase in performance by a date certain if the user continues to train per their training plan). Still further, the virtual athletic coach may be able to estimate a certain performance improvement relative to the user's stated goal(s). For example, the virtual athletic coach may estimate a 2-minute time reduction for a stated goal of running a marathon if the user continues to train per their training plan.

As discussed above, the operations 200 overall may be used to dynamically generate custom training plans for users of the virtual athletic coach. A training plan often involves first breaking a season down into different phases, with each phase focusing on specific abilities or limiters that are necessary for the athlete to achieve their stated goal(s). As such, each phase includes specific workouts along with specifications regarding how the training load should be distributed to the athlete. The following generating operation 250 combines the outputs of the fitness, fatigue, and/or performance predictors (outputs of operations 230, 235, 240) with the athlete's life constraints and stated goals to optimize each phase of the athlete's season, resulting in a dynamic training plan specific to the athlete's individual circumstances and stated goal(s). The fitness/fatigue/performance models determine the athlete's response to a given training stimulus to achieve the stated goal(s). The life constraints may be further divided into daily constraints and weekly constraints. In an example implementation, daily constraints define the athlete's availability to train in the different disciplines and time available to train for a given day. Each day is broken down into three periods, morning, noon, and evening, and each period can have 0-2 workouts scheduled. Weekly constraints define a weekly cap on the number of sessions to be performed in each discipline along with a maximum number of hours available to train for the week.

An inputting operation 245 inputs the fatigue profile, the fitness profile, the performance profile, the stated goals, and the life constraints into a user optimization engine. The user optimization engine contains a database of training plan options for the user. The user optimization engine balances the user's stated goals against their life constraints, taking into account the user's fatigue, fitness, and performance profiles to generate a training plan appropriate for the user. In some instances, the user optimization engine operates on only a subset of the fatigue profile, the fitness profile, the performance profile, the stated goals, and the life constraints as inputs.

A further generating operation 250 generates a training plan for the user to achieve the stated goals within the life constraints. The user optimization engine may utilize a variety of techniques to generate the training plan for the user. In one instance, the generating operation 250 utilizes a randomized optimization approach. Specifically, the generating operation 250 generates a predetermined number of random solutions defining the training plan that satisfy the user's life constraints. The generated number of random solutions are scored based on their projected effect on the user's fatigue, fitness, and performance profiles and the highest scoring solution is selected as the user's training plan. In this implementation, while the user optimization engine is prevented from considering all possible solutions, the predetermined number of random solutions is high enough that statistically at least one of the generated random solutions is likely a good option for the user. The subsequent scoring of the generated random solutions ensures that the at least one good option for the user is selected.

Further, the user optimization engine may utilize an iterative revising and rescoring process to fine tune the generated random solutions and optimize against the user's fatigue, fitness, and performance profiles. More specifically, the user optimization engine may score the randomly generated solutions, make small changes to the randomly generated solutions, keep a subset of the randomly generated solutions for the next iteration (e.g., keep the randomly generated solutions that meet a scoring threshold), and rescore the randomly generated solutions. This process may repeat until a singular revised solution remains, which is used to generate the user's training plan. In some cases, the revisions are directed specifically to complying with the user's life constraints so that the iterative changes revise the randomly generated solutions to meet the user's life constraints. Typically, once the iteration is complete, the remaining singular revised solution would comply with the user's life-constraints. In some cases, a negative score is applied to features of the randomly generated solutions that violate one or more of the user's life constraints to encourage selection of a singular revised solution that satisfies all of the user's life constraints.

In another implementation, the user optimization engine is forced to consider only valid solutions as defined by solutions that comply with the user's life-constraints. For example, if the user optimization engine randomly generated three solutions, two of which violate at least one of the user's life-constraints, features of the two randomly generated three solutions that violate the user's life-constraints would be automatically changed so that they comply with the user's life-constraints. As a result, all of the randomly generated solutions comply with the user's life-constraints and are then subsequently scored to determine a best option from a fatigue, fitness, and performance profile perspective from the randomly generated solutions. In an example implementation, one of a user's life-constraints is that the user is not available to work out on Wednesdays. As a result, all randomly generated solutions that include a workout for the user working on Wednesdays are automatically changed so that the user does not work out on Wednesday prior to scoring. In a simple example, this could be effected by deleting all Wednesday workouts. A similar life-constraint is that the user only wishes to work out three days per week. Any solutions that include four or more workouts have excessive workouts deleted from the solution prior to scoring. By modifying all solutions to comply with the user's life-constraints prior to scoring, a valid solution for the user is ensured regardless of the outcome of the iterative scoring.

In a further example implementation, a differential evolution algorithm is used. The differential evolution is a metaheuristic optimization algorithm (evolutionary programming). The algorithm may be implemented in the SciPy Python package, for example. The generating operation 250 utilizes a custom scoring function that evaluates candidate solutions and returns a weighted score based on four criteria: 1) improvement in fitness; 2) distribution of individual sessions; 3) distribution of training load amongst the chosen sports; and 4) distribution of intensity of workouts. A vectorized decoder decodes a sequence, scores it, and returns the associated training plan. The vectorized decoder uses the following non-exclusive list of potential variables:

availablePeriods: array[AvailablePeriod], where each item is an AvailablePeriod object that represents a single day and defines the daily constraints;

scheduledDays: hashMap[date: list[Workout], where Key is date of training day and Value is list of workouts scheduled by the user;

recoveryDays: set[date], a set of dates defining when recovery should be taken;

sportDistribution: array[SportDistribution], a target for distribution of training load amongst the various sports being trained for;

energyDistribution: array[EnergyDistribution], a target for distribution of training intensity amongst the predefined training zones;

weights: array[float], weights to be applied to the four scoring criteria;

workouts: array[Workout], all workouts assigned to the phase;

ffdCeiling: float, defines a maximum acceptable value for FFD;

ffdFloor: float, defines a minimum acceptable value for FFD;

metrics: hashMap, maintains record of daily training load for each sport;

dailyConstraint: DailyConstraint, checks to see if workouts violate daily constraints;

weeklyConstraint: WeeklyConstraint, checks to see if workouts violate weekly constraints; and sequence: array[float], a sequence of floating-point numbers to be decoded into training plan.

The vectorized decoder takes as input the above variables and utilizes a sequence, or array, of floating-point numbers in the range [0, 1). The sequence represents the training plan and has length equal to (the number of days in phase)×(the number of periods per day)×(the number of workouts per period). In an example having one period per day and two workouts per period, the sequence length is twice the number of days in the phase. To convert the sequence into a meaningful representation of workouts, the continuous, floating point numbers are converted into discrete workouts. This is done by splitting the [0, 1) interval into N bins, where N is the number of workouts assigned to the phase. Whichever bin an element of the sequence falls in is the index of the associated workout in the workouts array.

After converting the sequence, the workouts are analyzed by iterating through each day in the phase. At the beginning of each week, the weekly constraints are updated to include any workouts scheduled by the athlete. We initialize the schedule for the day to an empty list, which is populated by workouts if they do not violate any constraints. For example, if the day is not a race day and there are no scheduled workouts, the vectorized decoder analyzes the workouts from the sequence. The total training load for the day is used to calculate the CWL, AWL, and FFD discussed above. Then the workout is checked to see if it violates a daily constraint (discussed above), a weekly constraint (discussed above), or a FFD constraint. The FFD constraint defines that on regular training days, the FFD does not drop below the FFD floor. On recovery days, the FFD constraint defines that the FFD be increasing without going above the FFD ceiling.

If all constraints are satisfied, the workout is kept and added to the schedule. The CWL, AWL, and FFD are calculated for the training load of the workout and stored. If the workout does violate a constraint, it is discarded, and the CWL, AWL, and FFD are calculated with a training load of zero. By decoding the sequence in this manner, every solution is viable, a solution that violates any constraints is avoided. Further, by avoiding penalties, the search space for the vectorized decoder is smoothed. After the entire sequence has been decoded, it is scored. The following non-exclusive list of four contributing factors for scoring follow:

Variability: a measure of how spaced out the workouts are in each discipline. For example, if an athlete will swim twice per week, it is preferable to have 2-3 days between the workouts rather than swim two days in a row and then not again for five days;

CWL ramp rate: a measure of how quickly the CWL increases per 28 days. Improving fitness is generally a goal of training and is thus monitored accordingly. However, fitness should not increase too quickly. Training too much too quickly may result in a high CWL ramp rate, which can cause injury or illness;

Load distribution: a measure of how the training load is distributed among the different sports. A target distribution is defined in the phase itself, and this measures how close the actual distribution is to the target; and Energy distribution: a measure of how the intensity of the workouts is distributed. In endurance sports, the athlete may be trained at certain intensities in order to train specific energy sub-systems of the athlete's body. The target distribution is defined in the phase itself, and this measures how close the actual distribution is to the target.

Each factor is calculated and converted to be within a range of (e.g., 0-20), so that they are all on the same scale. A weight is then applied to each factor and the sum is taken. The differential evolution algorithm uses a minimization algorithm, so the negative of the sum of the factors is taken to be the final score for each solution.

Regardless of the technique used to score each of the generated array of solutions, once the generating operation 250 determines the best of the randomly generated solutions (e.g., via iterative revising and rescoring, forced compliance with the user's life constraints, and/or vectorized decoding), the selected solution is decoded to yield a user interpretable training plan that is presented to the user via the virtual athletic coach application.

Figure 3:
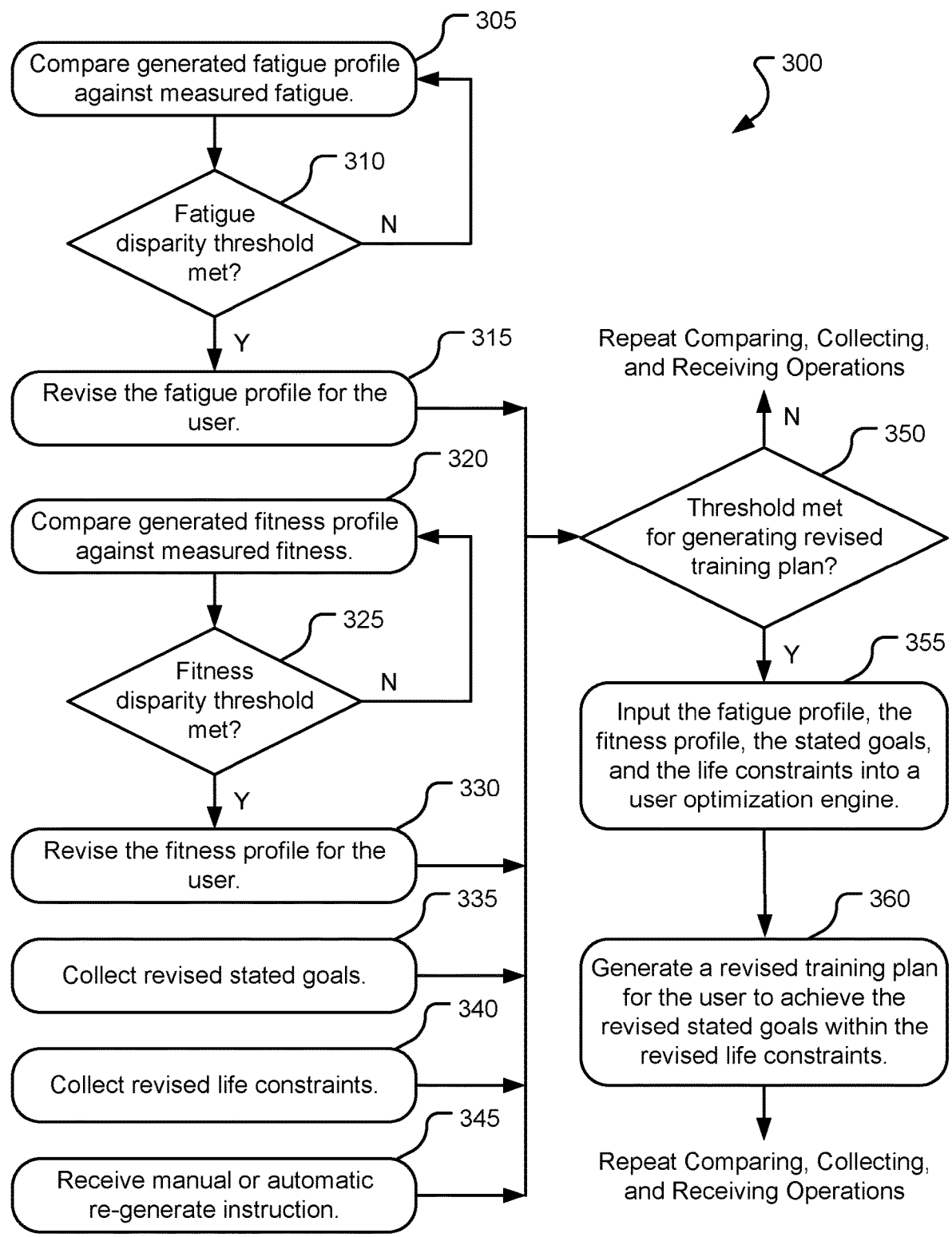
FIG. 3 illustrates example operations for revising a training plan for a user using a virtual athletic coach.

FIG. 3 illustrates example operations 300 for revising a training plan for a user using a virtual athletic coach. Operations 300 are performed using a virtual athletic coach optimization engine (see e.g., optimization engine 100 of FIG. 1) and a virtual athletic coach application (see e.g., user interface screenshots 400, 500, 600, 700, 800, 900 of FIGS. 4-9) following operations 200, which are used to generate a first training plan for the user. Operations 300 are generally used to evaluate the selected first training plan, determine if and when to determine a revised training plan, and then determine the revised training plan.

A first comparing operation 305 compares a previously generated fatigue profile for the user (see e.g., generating operation 230 of FIG. 2) against measured fatigue for the user. The virtual athletic coach may collect measured fatigue for the user manually, such as by receiving a 1-10 ranking of the user's perceived fatigue, and/or automatically from a wearable device (e.g., by a calculation of current fatigue using resting heartrate, peak heartrate, etc.). Decision 310 determines if a fatigue disparity threshold has been met. The fatigue disparity threshold is a measured disparity between expected fatigue per the previously generated fatigue profile and the currently measured fatigue for the user.

If the fatigue disparity threshold has not been met, the first comparing operation 305 and the decision operation 310 repeat iteratively to monitor the fatigue disparity threshold.

If the fatigue disparity threshold has been met, a first revising operation 315 revises the user's fatigue profile to more closely approximate the user's fatigue given the user's actual performance to a previously determined training plan and other non-training considerations affecting the user's fatigue (e.g., the user's work and/or personal life).

A second comparing operation 320 compares a previously generated fitness profile for the user (see e.g., generating operation 235 of FIG. 2) against measured fitness for the user. The virtual athletic coach may collect measured fitness for the user manually, such as by receiving a 1-10 ranking of the user's perceived fitness, and/or automatically from a wearable device (e.g., by a calculation of current fitness using resting heartrate, peak heartrate, etc.). Decision 325 determines if a fitness disparity threshold has been met. The fitness disparity threshold is a measured disparity between expected fitness per the previously generated fitness profile and the currently measured fitness for the user.

If the fitness disparity threshold has not been met, the second comparing operation 320 and the decision operation 325 repeat iteratively to monitor the fitness disparity threshold. If the fitness disparity threshold has been met, a second revising operation 330 revises the user's fitness profile to more closely approximate the user's fitness given the user's actual performance to a previously determined training plan and other non-training considerations affecting the user's fitness (e.g., the user's work and/or personal life).

A first collection operation 335 collects revised stated goals from the user. The revised stated goals collected in operation 335 may be the same or similar to the stated goals collected in operation 205 of FIG. 2, however, the user may change their stated goals over time. The user may then re-enter their revised stated goals in the virtual athletic coach application. A second collection operation 340 collects revised life constraints from the user. The revised life constraints collected in operation 340 may be the same or similar to the life constraints collected in operation 210 of FIG. 2, however, the user may change their life constraints over time. The user may then re-enter their revised life constraints in the virtual athletic coach application.

In some cases, a receiving operation 345 receives a manual or automatic re-generation instruction intended to trigger generation of a revised training plan. In a first instance, the user is presented with the option of generating a revised training plan. Should the user elect to have a revised training plan generated (e.g., via the virtual athletic coach application), the receiving operation 345 receives that instruction. In a second instance, the receiving operation 345 receives an automatic re-generation instruction intended to trigger generation of a revised training plan. The automatic re-generation instruction may occur after a predetermined period of time, for example.

A decision operation 350 receives one or more of the revised fatigue profile, the revised fitness profile, the revised stated goals, the revised life constraints, and the re-generation instruction and determines if a threshold has been met to generate a revised training plan. The threshold may vary widely. In one implementation, if any of a revised fatigue profile, a revised fitness profile, a revised stated goal, a revised life constraint, and a re-generation instruction is received, the threshold has been met. In another implementation, the decision operation 350 receives enforces a minimum time period between re-generation of the user's training plan and/or requires more than one of the revised fatigue profile, the revised fitness profile, the revised stated goals, the revised life constraints, and the re-generation instruction to be received. Further, not all of the revised fatigue profile, the revised fitness profile, the revised stated goals, the revised life constraints, and the re-generation instruction may be treated equally. For example, the revised fatigue profile and the revised fitness profile may not meet the threshold unless they vary significantly from the previous fatigue profile and the previous fitness profile, respectively, while the re-generation instruction may be acted upon without any threshold beyond receipt of the re-generation instruction.

If the threshold has not been met, the comparing operations 305, 320, the collecting operations 335, 340, and the receiving operation 345 continue. If the threshold has been met, an inputting operation 355 inputs the revised fatigue profile, the revised fitness profile, a revised performance profile (if applicable), revised stated goal(s), and revised life constraint(s) into a user optimization engine. For any of the fatigue profile, fitness profile, performance profile, stated goal(s), and life constraint(s) that have not been revised, a previous fatigue profile, fitness profile, performance profile, stated goals, and/or life constraints may be re-utilized in the inputting operation 355. The inputting operation 355 may subsequently operate much the same way as the inputting operation 245 of FIG. 2, as described above.

A generating operation 360 generates a revised training plan for the user to achieve the revised (or previous, as applicable) stated goals within the revised (or previous, as applicable) life constraints. The generating operation 360 may generate the revised training plan in much the same way as the generating operation 250 of FIG. 2, as described above. The comparing operations 305, 320, the collecting operations 335, 340, and the receiving operation 345 continue such that the operations 300 repeat iteratively to generate revised training plans for the user over time when appropriate.

Figure 4:
FIG. 4 illustrates an example Personal Information user interface screenshot for a virtual athletic coach application.

FIG. 4 illustrates an example Personal Information user interface screenshot 400 for a virtual athletic coach application. The depicted interface is accessed by selecting the Personal Information tab 405, and a variety of personal information fields are presented for the user to fill out (e.g., Photo, First Name, Last Name, Nickname, Date of Birth, Gender, Physical Location, Athlete/Coach selector, Preferred System of Measurement, Height, Weight, and Resting Heart Rate). When the user has entered personal information into or revised any or all of the fields, the user may select the SAVE button 410 to save the entered (or revised) personal information.

FIG. 4 illustrates only a sample of the personal information that the virtual athletic coach may collect from a user using the Personal Information tab 405. Some or all of the collected information may be used as health data, as described above with reference to health data source(s) 108 of FIG. 1. Other information may be to identify the user to the virtual athletic coach application.

Figure 5:
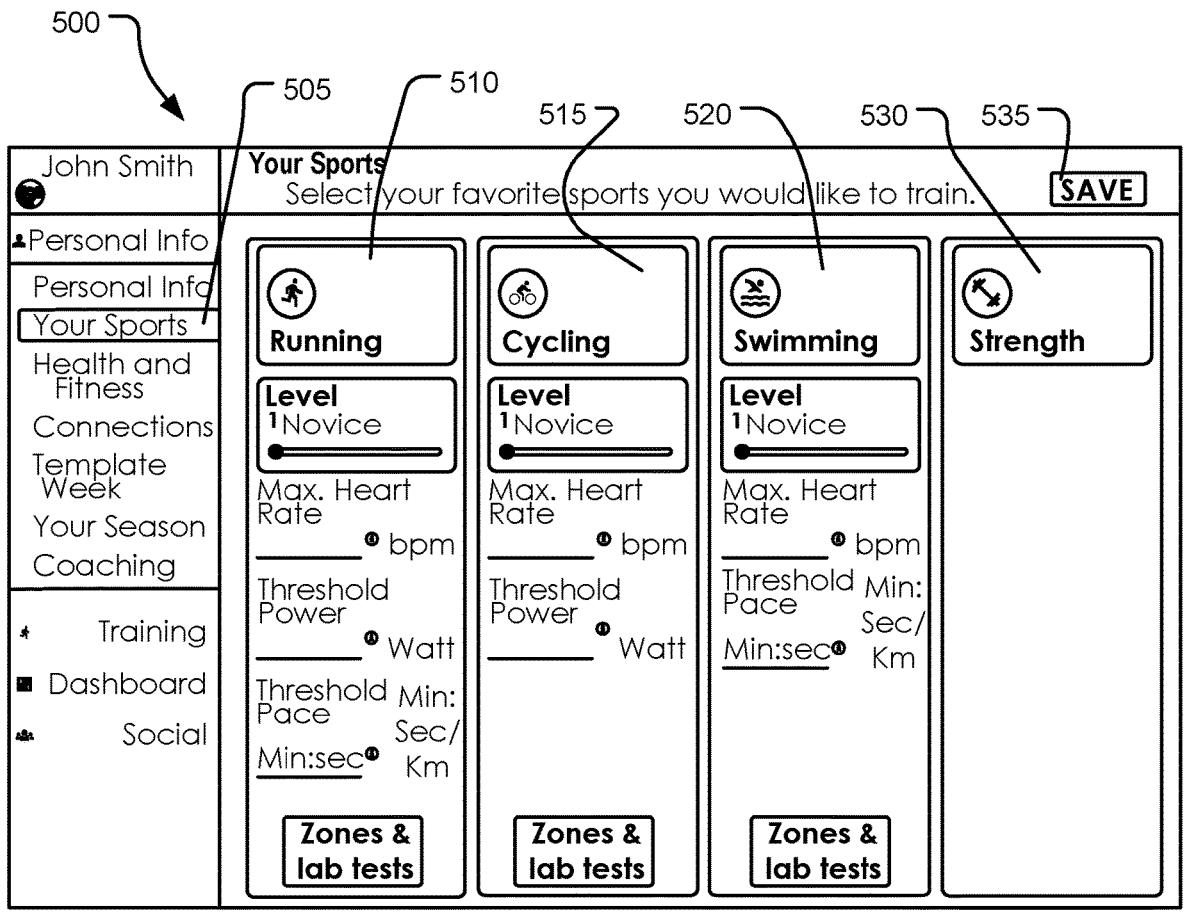
FIG. 5 illustrates an example Your Sports user interface screenshot for a virtual athletic coach application.

FIG. 5 illustrates an example Your Sports user interface screenshot 500 for a virtual athletic coach application. The depicted interface is accessed by selecting the Your Sports tab 505, and a variety of available sports for training purposes are presented to the user (here, Running 510, Cycling 515, Swimming 520, and Strength training 525. The user may select one or more of the available sports and enter user specific information regarding the user's performance in that sport (e.g., skill level, max heart rate, threshold power, and/or threshold pace). The user may also enter Zones & lab test information regarding the user's performance in each sport. When the user has entered their desired sport information into or revised any or all of the fields, the user may select the SAVE button 535 to save the entered (or revised) sport information.

FIG. 5 illustrates only a sample of the available sports and related information presented to the user via the Your Sports tab 505 that the virtual athletic coach may utilize to create a training plan for the user. Some or all of the collected information may be used as workout data and/or life constraints as described above with reference to workout data source(s) 110 and/or life constraint source(s) 112 of FIG. 1, for example.

Figure 6:
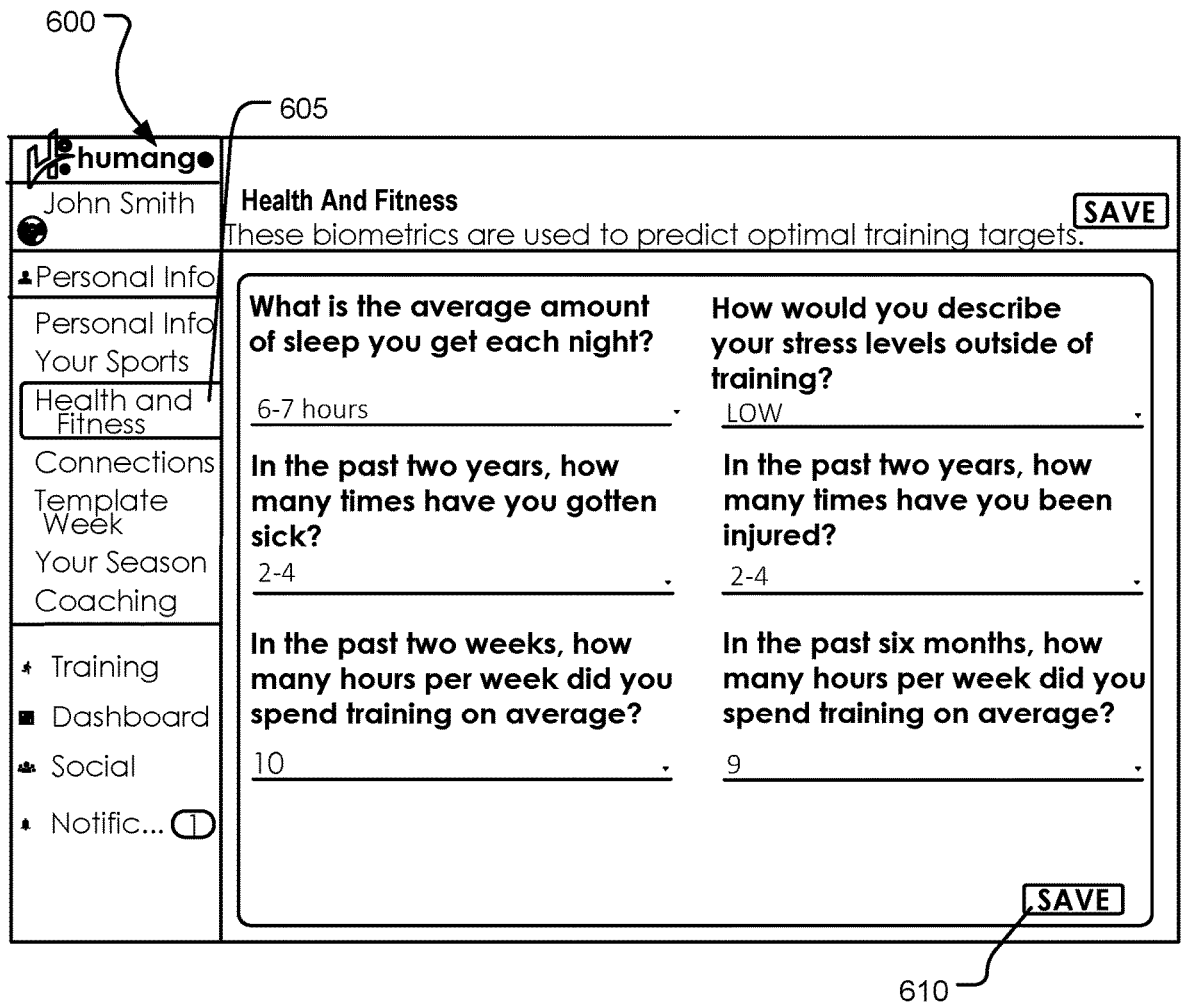
FIG. 6 illustrates an example Health And Fitness user interface screenshot for a virtual athletic coach application.

FIG. 6 illustrates an example Health And Fitness user interface screenshot 500 for a virtual athletic coach application. The depicted interface is accessed by selecting the Health And Fitness tab 605, and a variety of biometric questions are presented for the user to fill out (e.g., What is the average amount of sleep you get each night?; How would you describe your stress levels outside of training?; In the past two years, how many times have you gotten sick?; In the past two years, how many times have you been injured?; In the past two weeks, how many hours per week did you spend training on average?; In the past six months, how many hours per week did you spend training on average). When the user has entered their responses into or revised any or all of the fields, the user may select the SAVE button 610 to save the entered (or revised) Health And Fitness responses.

FIG. 6 illustrates only a sample of the biometric questions that may be presented to the user using the Health And Fitness tab 605. Some or all of the collected responses may be used as health data, workout data, life constraints, and/or stated goal(s) as described above with reference to health data source(s) 108, workout data source(s) 110, life constraint source(s) 112, and/or stated goal(s) 118 of FIG. 1, for example.

Figure 7:
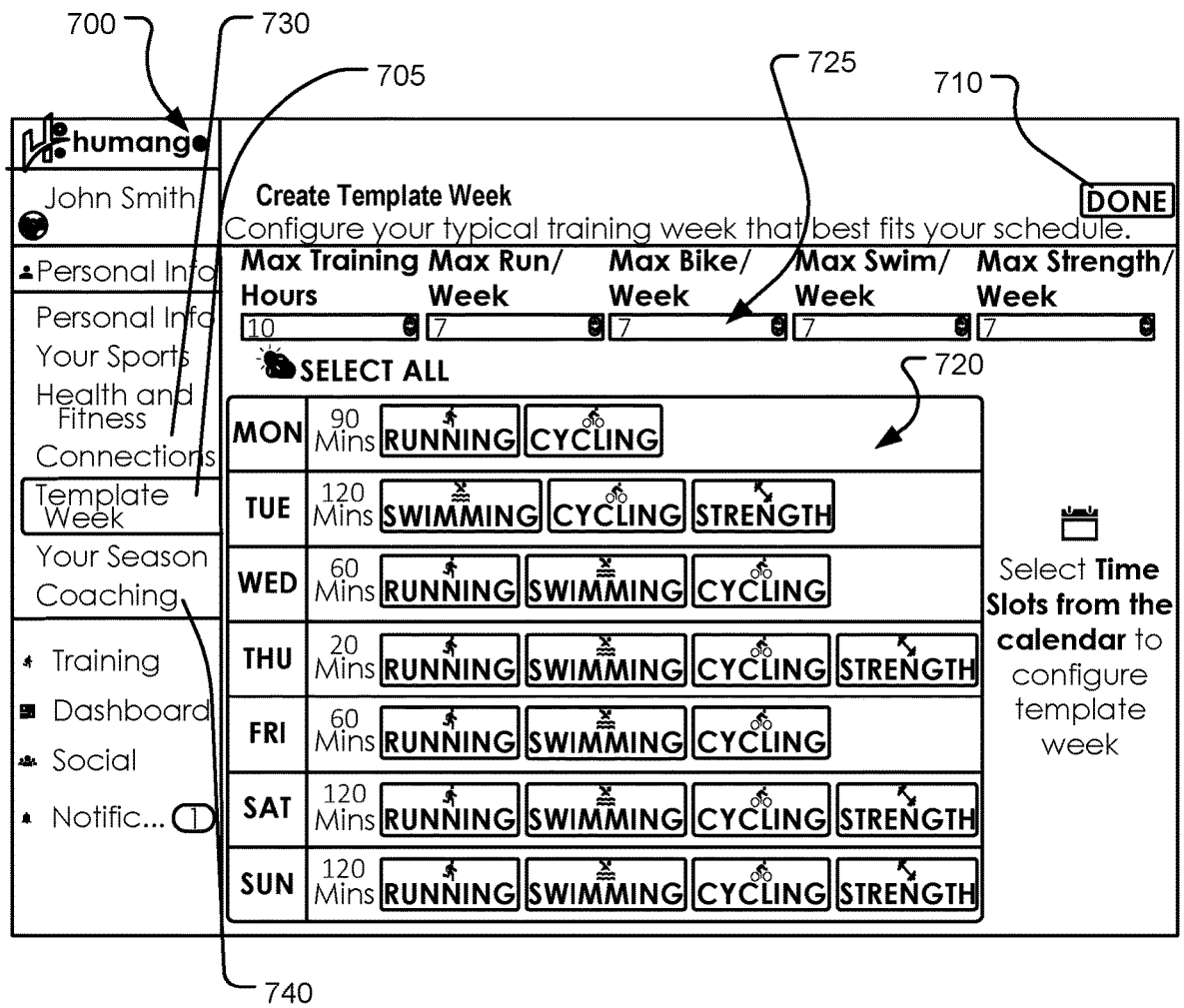
FIG. 7 illustrates an example Template Week user interface screenshot for a virtual athletic coach application.

FIG. 7 illustrates an example Template Week user interface screenshot 700 for a virtual athletic coach application. The depicted interface is accessed by selecting the Template Week tab 705, and a sample week 720 with the ability to add and edit combinations of available sports and durations for each day is provided to the user. The user is further provided options for entering life constraints 725 specific to the available sports and durations (e.g., Maximum Training Hours, Maximum Runs Per Week, Maximum Cycling Sessions Per Week, Maximum Swimming Sessions Per Week, and Maximum Strength Training Sessions Per Week). When the user has entered or revised the template training week and any desired life constraints thereon, the user may select the DONE button 710 to save the entered (or revised) template training week and life constraints.

FIG. 7 illustrates only a sample of the available sports and durations for each day, as well as life constraints 725 that may be presented to the user using the Template Week tab 705. Some or all of the collected responses may be used as health data, workout data, and/or life constraints as described above with reference to health data source(s) 108, workout data source(s) 110, and/or life constraint source(s) 112 of FIG. 1, for example.

FIG. 7 also illustrates additional tabs (Connections tab 730 and Coaching tab 740) that may be selected by the user. The Connections tab 730 presents the user an opportunity to connect the virtual athletic coach application to one or more devices (e.g., one or more wearable devices to collect biometric data regarding the user). The Connections tab 730 may also present a summary of the information currently and/or previously collected by the user's connected devices. The Your Season tab 735 presents the user a summary of their current athletic season using the virtual athletic coach. The Coaching tab 740 is an interface specific to use of the virtual athletic coach with the user being a human coach. The Coaching tab 740 may provide the human coach user access to information regarding another athlete user that the human coach user is training.

Figure 8:
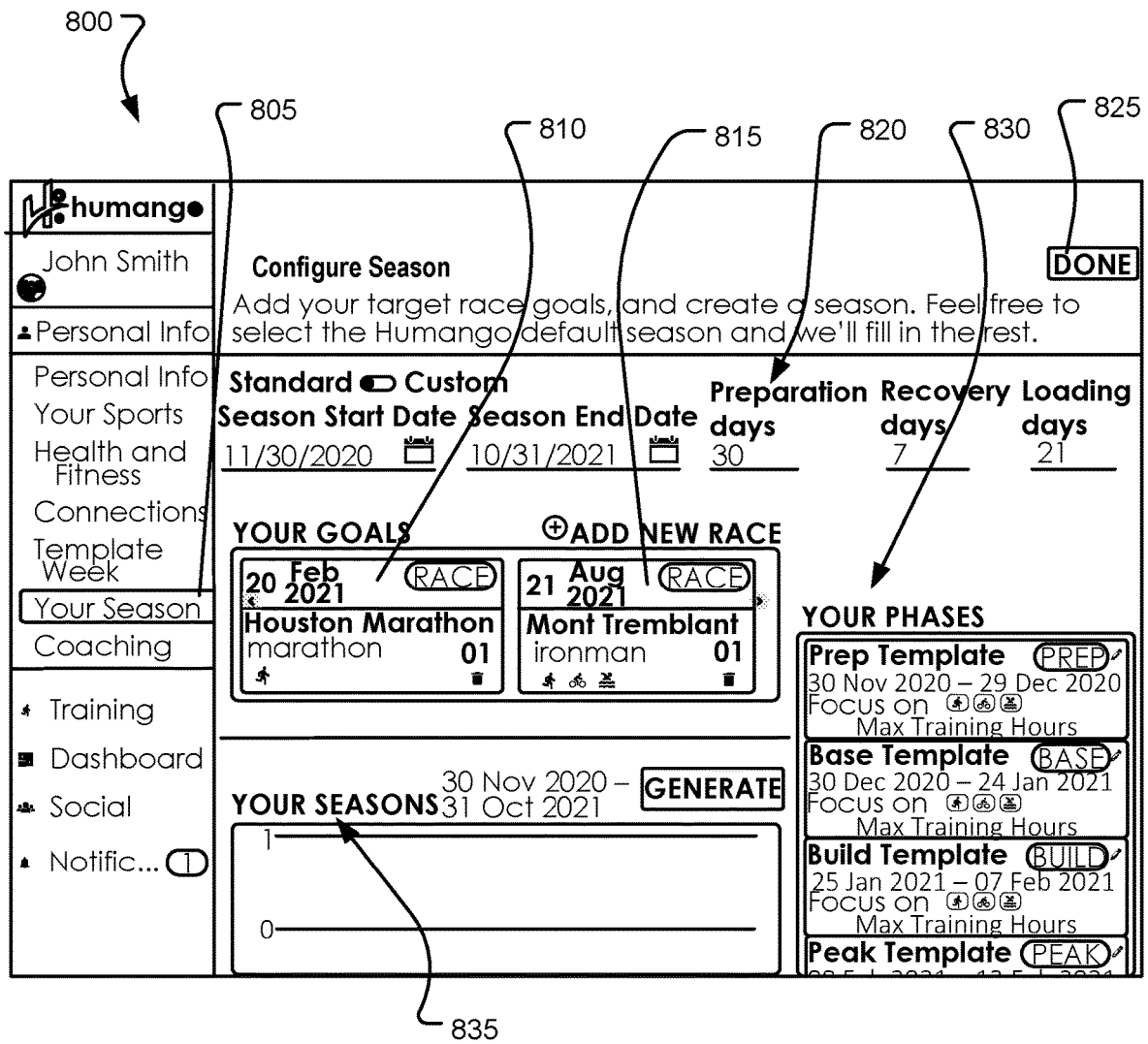
FIG. 8 illustrates an example Your Season user interface screenshot for a virtual athletic coach application.

FIG. 8 illustrates an example Your Season user interface screenshot 800 for a virtual athletic coach application. The depicted interface is accessed by selecting the Your Season tab 805, and the user is presented with the option to add stated goals (Your Goals, here, the Houston Marathon 810 on February 2021 and the Mont Tremblant Ironman 815 on Aug. 21, 2021). The user is also presented with a season customizer 820. Here, the user has defined that their season runs from Nov. 30, 2020 to Oct. 31, 2021 and the user has 30 preparation days and 7 recovery days, with 21 loading days per 28-day period. Further, the user is presented with a training phase customizer 830 (You Phases, here, listing Prep, Build, Base, and Peak templates that allow the user to customize their training phases). Still further, the Your Season tab 805 includes Your Seasons historical information 835 that will present the user with information regarding the user's prior seasons using the virtual athletic coach application. When the user has entered or revised their stated goals and made any desired customizations to their season and training phases, the user may select the DONE button 825 to save the entered (or revised) stated goals and season and training phase customizations.

FIG. 8 illustrates only a sample of the possible Stated Goals and Season/Training Phase customizations that may be presented to the user using the Your Season tab 805. Some or all of the collected responses may be used as life constraints, and/or stated goal(s) as described above with reference to life constraint source(s) 112 and/or stated goal(s) 118 of FIG. 1, for example.

Figure 9:
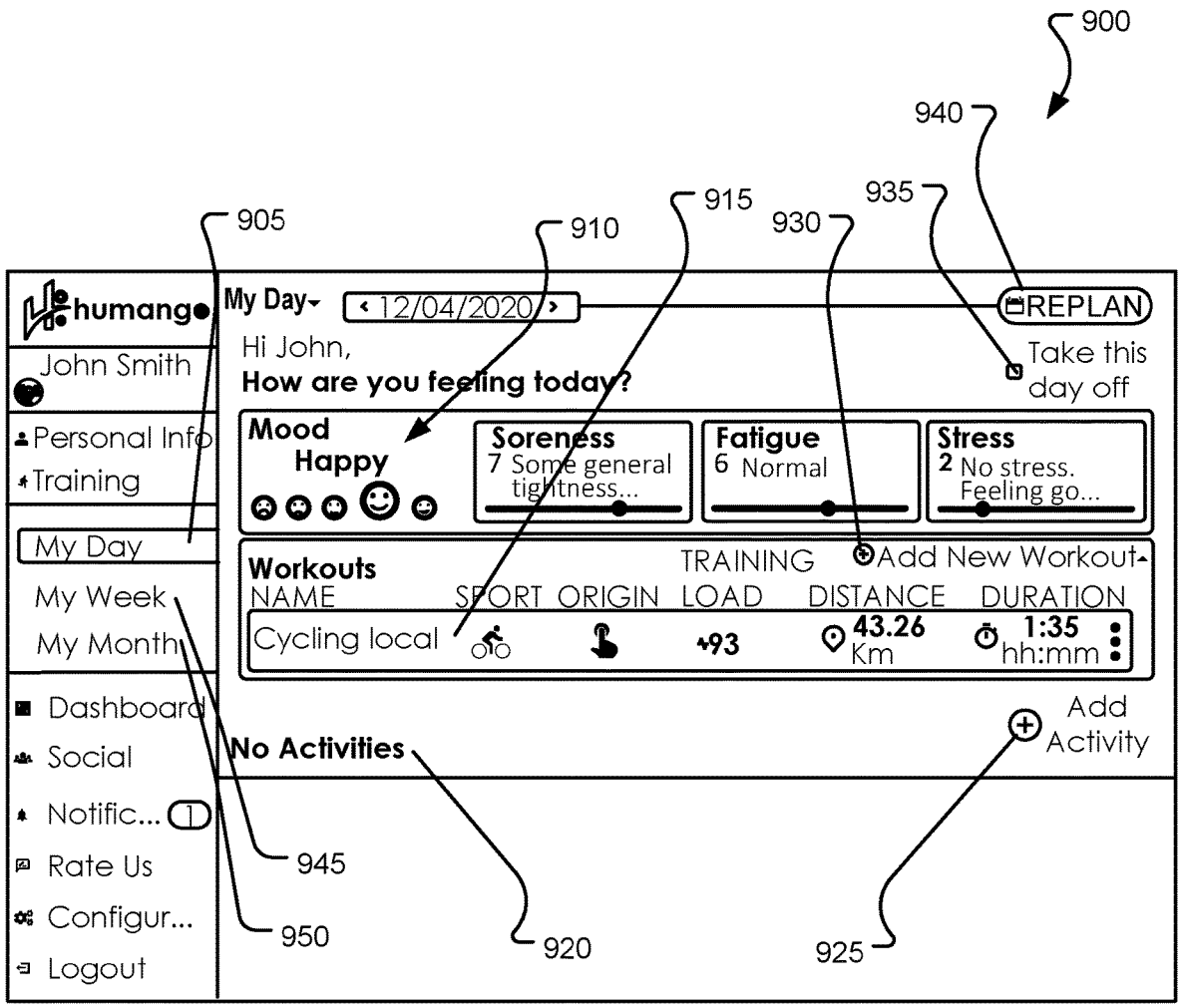
FIG. 9 illustrates an example My Day user interface screenshot for a virtual athletic coach application.

FIG. 9 illustrates an example My Day user interface screenshot 900 for a virtual athletic coach application. The depicted interface is accessed by selecting the My Day tab 905, and the user is presented with a summary of their training day (here, Dec. 4, 2020). A Mood interface 910 permits the user to enter information contributing to their mood for the day (e.g., 1-10 rankings of the user's Soreness (7/10), Fatigue (6/10), and Stress (2/10), yielding an overall Mood of "Happy"). Data collected using the Mood interface 910 may be interpreted as measured fitness and/or fatigue for the purposes of comparing against calculated fitness and/or fatigue (see e.g., comparing operations 305, 315 of FIG. 3).

The user is further presented with a listing of today's workouts 915 (here, a local cycling workout that was already completed in 1 hour, 35 minutes). Additional completed or to-be completed workouts scheduled for Dec. 4, 2020 will be listed in today's workouts 915 as well. The user may also add a workout using the Add Workout selector 930. The user is still further presented with a listing of today's activities 920 (here, none). The activities 920 may include other physical activities that the user may accomplish on Dec. 4, 2020, but are not explicitly workouts and are not part of the user's training plan. The user may add an activity using the Add Activity selector 925.

In some cases, the user may elect to take a day off of their training plan. The Take This Day Off selector 935 allows the user to indicate to the virtual athletic coach application that they are taking the day off. The user may also elect to manually trigger regeneration of their training plan (see e.g., operation 345 of FIG. 3) by triggering the Replan selector 940. FIG. 9 also illustrates additional tabs (My Week tab 945 and My Month tab 950) that may be selected by the user. In various implementations, the My Week tab 945 and My Month tab 950 each provide similar information as the depicted interface for the My Day tab 905, but in weekly and monthly timescales, respectively.

Figure 10:
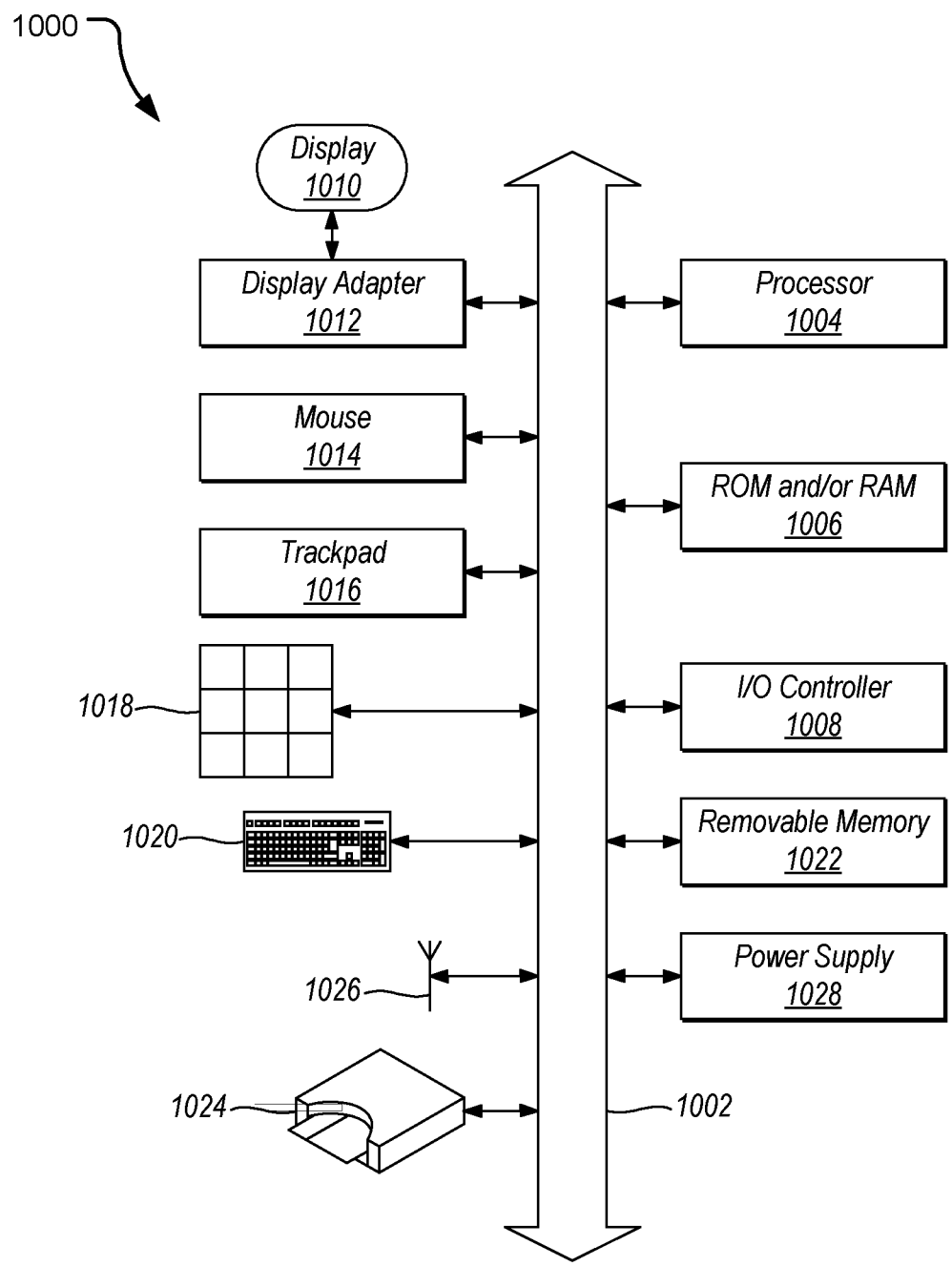
FIG. 10 illustrates an example system diagram of a computer system suitable for implementing aspects of an optimization engine for a virtual athletic coach.

FIG. 10 illustrates an example system diagram of a computer system 1000 suitable for implementing aspects of a virtual athletic coach optimization engine and a virtual athletic coach application (collectively a virtual athletic coach). System 1000 includes a bus 1002 which interconnects major subsystems such as a processor 1004, internal memory 1006 (such as random-access memory (RAM) and/or read-only memory (ROM)), an input/output (I/O) controller 1008, removable memory (such as a memory card) 1022, and external devices such as display screen 1010 via display adapter 1012, a mouse 1014, a trackpad 1016, a numeric keypad 1018, an alphanumeric keyboard 1020, a smart card adapter or acceptance device 1024, a wireless antennae or other interface 1026, and a power supply 1028. Many other devices can be connected. Wireless interface 1026 together with a wired network interface (not shown), may be used to interface to a local or wide area network (such as the Internet) using any network interface system known to those skilled in the art.

Many other devices or subsystems (not shown) may be connected in a similar manner (e.g., servers, personal computers, tablet computers, smart phones, mobile devices, etc.). Also, it is not necessary for all of the components depicted in FIG. 10 to be present to practice the presently disclosed technology. Furthermore, devices and components thereof may be interconnected in different ways from that shown in FIG. 10. Code to implement the presently disclosed technology may be operably disposed in the internal memory 1006 or stored on storage media such as the removable memory 1022, a thumb drive, a CompactFlash® storage device, a DVD-R ("Digital Versatile Disc" or "Digital Video Disc" recordable), a DVD-ROM ("Digital Versatile Disc" or "Digital Video Disc" read-only memory), a CD-R (Compact Disc-Recordable), or a CD-ROM (Compact Disc read-only memory). For example, in an implementation of the computer system 1000, code for implementing the virtual athletic coach described in detail above may be stored in the internal memory 1006 and configured to be operated by the processor 1004.

Aspects of the virtual athletic coach optimization engine and the virtual athletic coach application (collectively, the virtual athletic coach) may be implemented in a tangible computer-readable storage media readable by a computer. The term "tangible computer-readable storage media" includes, but is not limited to, random access memory ("RAM"), ROM, EEPROM, flash memory or other memory technology, CDROM, digital versatile disks (DVD) or other optical disk storage, magnetic cassettes, magnetic tape, magnetic disk storage or other magnetic storage devices, or any other tangible medium which can be used to store the desired information, and which can be accessed by mobile device or computer. In contrast to tangible computer-readable storage media, intangible computer-readable communication signals may embody computer readable instructions, data structures, program modules, or other data resident in a modulated data signal, such as a carrier wave or other signal transport mechanism.

The embodiments described herein are implemented as logical steps in one or more computer systems. The logical operations of the present invention are implemented (1) as a sequence of processor-implemented steps executing in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects, or modules. Furthermore, it should be understood that logical operations may be performed in any order, adding or omitting operations as desired, unless explicitly claimed otherwise or a specific order is inherently necessitated by the claim language.

The above specification, examples, and data provide a complete description of the structure and use of exemplary embodiments of the invention. Since many embodiments of the invention can be made without departing from the spirit and scope of the invention, the invention resides in the claims hereinafter appended. Furthermore, structural features of the different embodiments may be combined in yet another embodiment without departing from the recited claims.

What is claimed is:

1. A method of providing virtual athletic coaching comprising:
    generating, using a computer, a fatigue profile that tracks and projects a user's fatigue over time;
    generating, using the computer, a fitness profile that tracks and projects the user's fitness over time;
    collecting stated goals and life constraints from the user;
    inputting the fatigue profile, the fitness profile, the stated goals, and the life constraints into an optimizer, the optimizer to combine the inputs to optimize a training plan for the user using artificial intelligence; and
    generating with the optimizer and using the computer, the training plan for the user to achieve the stated goals within the life constraints based on the fatigue profile and the fitness profile.

2. The method of claim 1, further comprising:
    collecting health data from the user; and
    collecting workout data from the user, wherein one or both of the fatigue profile and the fitness profile are based on the collected health data and workout data.

3. The method of claim 2, further comprising:
    cleansing the health data and the workout data prior to generating the fatigue profile and the fitness profile for the user.

4. The method of claim 1, further comprising:
    generating, using the computer, a performance profile that tracks and projects the user's performance over time, wherein the training plan is further to optimize the performance profile to achieve the stated goals.

5. The method of claim 4, further comprising:
    outputting a projected performance metric for the user relative to the stated goals.

6. The method of claim 1, further comprising:
    comparing the generated fatigue profile for the user against measured user fatigue;
    revising the fatigue profile for the user based on the measured user fatigue;
    comparing the generating a fitness profile for the user against measured user fitness;
    revising the fitness profile for the user based on the measured user fitness;
    inputting the revised fatigue profile and the revised fitness profile into the user optimization engine; and generating, using the computer, a revised training plan for the user to achieve the stated goals within the life constraints based on the revised fatigue profile and the revised fitness profile.

7. The method of claim 6, wherein the comparing and revising operations are performed in response to one of a user direction and expiration of a predetermined time period.

8. The method of claim 6, wherein the comparing and revising operations are performed periodically and the revised training plan is generated when one or both of:
the revised fatigue profile diverges from the fatigue profile beyond a predetermined fatigue threshold; and
the revised fitness profile diverges from the fitness profile beyond a predetermined fitness deviation threshold.

9. The method of claim 1, further comprising:
collecting revised stated goals from the user;
inputting the revised stated goals into the user optimization engine; and
generating, using the computer, a revised training plan for the user to achieve the revised stated goals within the life constraints.

10. The method of claim 1, further comprising:
collecting revised life constraints from the user;
inputting the revised life constraints into the user optimization engine; and
generating, using the computer, a revised training plan for the user to achieve the stated goals within the revised life constraints.

11. The method of claim 1, wherein the training plan is generated using a randomized optimization approach.

12. The method of claim 11, wherein the generating operation includes:
generating, using the computer, a number of random training plan solutions;
scoring the generated training plan solutions in projected capability to achieve the stated goals within the life constraints based on the fatigue profile and the fitness profile;
selecting a subset of the scored training plan solutions that meet a score threshold;
re-scoring the selected subset of the scored training plan solutions; and
selecting a highest scoring one of the re-scored training plan solutions as the generated training plan for the user.

13. The method of claim 12, wherein the generating training plan solutions are each forced to comply with the user's life constraints prior to the scoring operation.

14. The method of claim 1, wherein the user is an athlete.

15. A virtual athletic coach comprising:
a fatigue predictor to generate a fatigue profile that tracks and projects a user's fatigue over time using a computer;
a fitness predictor to generate a fitness profile that tracks and projects the user's fitness over time using the computer; and
an optimizer to receive the fatigue profile from the fatigue predictor, the fitness profile from the fitness predictor, and stated goals and life constraints from the user and combine the inputs to optimize a training plan for the user using artificial intelligence and the computer, the training plan to achieve the stated goals within the life constraints based on the fatigue profile and the fitness profile.

16. The virtual athletic coach of claim 15, further comprising:
a performance predictor to generate a performance profile that tracks and projects the user's performance over time using the computer, wherein the training plan is further to optimize the performance profile to achieve the stated goals.

17. One or more tangible computer-readable storage media encoding computer-executable instructions for executing on a computer system a computer process for providing virtual athletic coaching, the computer process comprising:
generating a fatigue profile that tracks and projects a user's fatigue over time;
generating a fitness profile for a user that tracks and projects the user's fitness over time;
collecting stated goals and life constraints from the user;
inputting the fatigue profile, the fitness profile, the stated goals, and the life constraints into an optimizer, the optimizer to combine the inputs to optimize a training plan for the user using artificial intelligence; and
generating with the optimizer the training plan for the user to achieve the stated goals within the life constraints based on the fatigue profile and the fitness profile.

18. The tangible computer-readable storage media of claim 17, wherein the computer process further comprises:
collecting health data from the user; and
collecting workout data from the user, wherein one or both of the fatigue profile and the fitness profile are based on the collected health data and workout data.

19. The tangible computer-readable storage media of claim 18, wherein the computer process further comprises:
cleansing the health data and the workout data prior to generating the fatigue profile and the fitness profile for the user.

20. The tangible computer-readable storage media of claim 17, wherein the computer process further comprises:
generating a performance profile that tracks and projects the user's performance over time, wherein the training plan is further to optimize the performance profile to achieve the stated goals.

* * * * *